United States Patent [19]

Chiba et al.

[11] Patent Number: 4,730,925
[45] Date of Patent: Mar. 15, 1988

[54] METHOD OF SPECTROSCOPICALLY DETERMINING THE COMPOSITION OF MOLTEN IRON

[75] Inventors: Koichi Chiba; Akihiro Ono, both of Kawasaki; Takamasa Ohno, Sakai; Masaki Okajima, Sakai; Hiroshi Yamane, Sakai; Minoru Hayata, Sakai, all of Japan

[73] Assignee: Nippon Steel Corporation, Tokyo, Japan

[21] Appl. No.: 905,330

[22] Filed: Sep. 9, 1986

[30] Foreign Application Priority Data

Sep. 20, 1985 [JP] Japan .................................. 60-207975
Dec. 28, 1985 [JP] Japan .................................. 60-293658

[51] Int. Cl.$^4$ ...................... G01N 21/71; G01N 21/72
[52] U.S. Cl. .................................. 356/311; 250/341; 250/372; 356/315
[58] Field of Search ................. 356/36, 311, 313, 315, 356/417; 250/340, 341, 372

[56] References Cited

FOREIGN PATENT DOCUMENTS 56-145336 11/1981 Japan .
58-102137 6/1983 Japan .
59-157541 9/1984 Japan .
60-162943 8/1985 Japan .
60-162944 8/1985 Japan .
60-162945 8/1985 Japan .
60-219538 11/1985 Japan .
1116052 6/1968 United Kingdom .

Primary Examiner—Vincent P. McGraw
Attorney, Agent, or Firm—Wenderoth, Lind & Ponack

[57] ABSTRACT

Oxygen or a mixed gas containing oxygen, or a chemical flame produced by a mixture of a combustion gas and a combustion-assisting gas containing oxygen, is blown against the surface of molten iron to cause radiation emission. The radiations are divided into components of different wavelengths, and the resulting emission spectra are measured to determine the composition of the molten iron.

9 Claims, 5 Drawing Figures

METHOD OF SPECTROSCOPICALLY DETERMINING THE COMPOSITION OF MOLTEN IRON

BACKGROUND OF THE INVENTION

1. Field of the Invention

This invention relates to a method of determining the contents in percentage of constituents in molten iron by measuring the emission spectrum produced at the surface thereof. The method according to this invention is applicable, for example, to the analysis of constituents of molten iron contained in a basic oxygen converter.

2. Description of the Prior Art

For proper control of such operations as metal refining and steelmaking processes, it is necessary to grasp the contents of constituents in the metal being processed through quick analysis and take necessary corrective measure, if needed, based on the obtained analytical data. To permit such an approach, various types of quick-analysis methods have been proposed and put to use for many analytical activities for process and quality control in steel and other metal industries.

For such analyses intended for the control of metal production processes, spark spectroscopy has been widely employed, in which solid block specimens prepared from sampled molten metal are used. But in recent years, the steel industry, for instance, has come to feel the need of achieving faster control techniques for conventional production processes and, at the same time, developing new controlling methods suited to many new production processes such as a steelmaking technique involving multistage refining. As such, there have been increasing need for the development of on-line real-time analysis techniques dealing directly with such molten metals as molten iron and steel.

With such purposes in mind, several spectroscopic techniques have been studied; some examples of which include a method that turns molten metal into fine powder using a special-purpose atomizer that uses argon gas and introduces the obtained powder to an emission spectrometer (BISRA Annual Report: 78(1966), 65, 78(1967), 35(1968)) and a method that identifies constituents of molten steel by optically detecting the absorption spectrum of constituents contained in gases released therefrom (Japanese Provisional Patent Publication No. 145336-1981). But these new techniques have been only tested on laboratory scale, not yet having been put to commercial use.

The inventors, too, have developed methods of spectroscopically analyzing fine particles containing representative constituents of molten metal that are vaporized by excitation through the passing of such electric discharge as plasma arc and spark or the irradiation of laser beams to molten metal (Japanese Patent Application Nos. 201154-1981 and 30879-1983) and methods of spectroscopically analyzing fine particles vaporized, and collected, from the surface of molten metal on the introduction of an inert gas from the top of a hermetically sealed vessel, at the bottom of which molten metal is captured (Japanese Patent Applications Nos. 16965-1984, 16966-1984, 16967-1984 and 75034-1984), with patent pending.

In the aforementioned methods, however, uniform clearance must be kept between the surface of molten metal and the tip of an excitation source such as a spark discharging electrode. Also, part of the apparatus must be immersed in molten metal. But molten meta, more often than not, is stirred or agitated, undergoes bath level fluctuations and flows in streams. Consequently, means to control or follow such variations should be provided. Where part of the apparatus (such as a probe) is brought in contact with or immersed in molten metal, the need of preventing the damage and erosion of the probe by the attack of the molten metal and protecting the probe from the chemical reaction between itself and the molten metal arises. In practice, however, violent changes in the metal bath level are hardly followed satisfactorily in the conventional spectroscopical methods employing spark and laser excitation. With the methods in which fine particles are collected by means of sampling probe immersed in molten metal, on the other hand, it has been difficult to keep the probe immersed in a stable condition without getting damaged where the molten metal is stirred or flows in streams.

SUMMARY OF THE INVENTION

This invention is aimed at accomplishing the aforementioned type of molten metal analysis without contacting the metal and in a short time. This invention is also aimed at performing on-line real-time analysis in such processes as metal refining and steelmaking.

This invention provides a practical method of spectroscopically determining constituents of molten iron without contacting it, in which analysis is conducted at a hot spot that appears when oxygen or a mixed gas containing oxygen is blown against the surface of the molten metal. As such, the molten iron analysis technique according to this invention is totally different from conventional ones.

When a basic oxygen converter is blown with oxygen or a mixed gas containing oxygen, a high-temperature region known as the "hot spot" appears, as has been known, at the surface of molten steel contained therein, as a result of the combustion of carbon and iron through the reaction with the blown oxygen gas. The temperature in the hot spot reaches, for example, approximately 2500° C. when oxygen is blown at a rate of 170 m$^3$/h.t against molten iron containing about 3 percent of carbon. The inventors discovered that some constituents of molten iron emit rays of light in the hot spot where the temperature is higher than in the rest. This is because such constituents are thermally vaporized under the extremely strong heat in the hot spot and part of the vaporized constituents are then excited to give emission spectra.

This invention is based on the discovery that constituents of molten iron can be spectroscopically determined by measuring emission spectra from the hot spot. This invention provides a spectroscopic method of directly determining constituents of molten iron which uses a hot spot, which appears when oxygen or mixed gases consisting of a combination of oxygen with argon, nitrogen, carbon dioxide, carbon monoxide, hydrocarbon gas or the like are blown against the surface of the molten iron, as a source of excitation.

The invention provides a practical method of spectroscopically determining constituents of molten iron without contacting it, in which a limited spot that is locally heated, as with the hot spot mentioned previously, when a chemical flame, such as an air-acetylene flame, is blown against the surface of the molten iron. When such chemical flames are blown against the surface of molten iron, part of the molten iron is locally heated thereby. In such a localized region, some constituents of the molten iron are thermally vaporized, with some portion of the vaporized constituents becoming excited to give emission spectra when captured by the chemical flame. The direct spectroscopic method according to this invention determines constituents of molten iron by causing emission of radiations and measuring the resulting emission spectra as mentioned previously.

The chemical flame used in the methods of this invention is formed by igniting a mixture of a combustion gas and combustion-assisting gas containing oxygen. An air-acetylene flame, air-propane flame, air-city gas flame, air-hydrogen flame, oxy-acetylene flame, nitrogen suboxide-acetylene flame, oxy-cyanogen flame, nitrogen oxide-acetylene flame, and nitrogen peroxide-acetylene flame are some examples.

Accordingly, the spectroscopic analyses according to this invention can be implemented with simpler apparatus, compared to conventional techniques in which spark discharge and laser beam are used as a source of excitation. The analyzing instruments are kept out of contact with molten iron whose constituents are being sought. The surface of molten iron is stabilized by blowing oxygen, a mixed gas containing oxygen or a chemical flame thereagainst. Consequently, direct on-line real-time spectroscopic analysis is practicable even where the molten iron is stirred or the bath level varies, such as in a basic oxygen converter at blow.

This invention eliminates such troublesome preparatory steps as sampling, cooling and solidification, cutting and grinding that have been necessitated by conventional methods applied to the analysis of molten iron. The resulting direct on-line real-time analysis is very useful for the control of such operations as metal refining and steelmaking processes.

DESCRIPTION OF THE PREFERRED EMBODIMENTS

Figure 1:
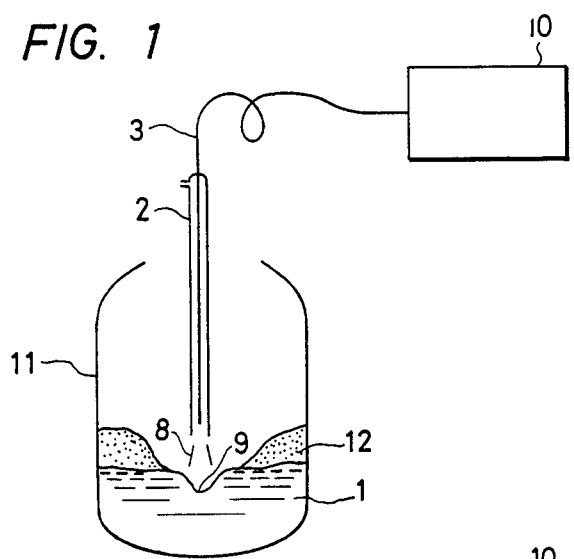
FIG. 1 is a cross-sectional view of a preferred embodiment of this invention that is operated using a lance.

The emission spectra from a hot spot comprise continuous spectra resulting from the infrared radiation from molten iron and emission spectra produced by constituents of the molten iron. The continuous spectra are identified as background radiation in spectroscopic analysis. The determined emission spectrum can be expressed by the following equation.

$$I_{abs} = I_{IR} + I_M$$

$$= (2\pi hc^2/\lambda^5)\exp(-hc/k\lambda T) + C \cdot \gamma(T) \cdot$$

-continued $$\phantom{= } P(T)\exp(-hc/k\lambda T)$$

$$= \{2\pi hc^2/\lambda^5 + C \cdot \gamma(T) \cdot P(T)\} \exp(-ch/k\lambda T)$$

where
$I_{abs}$: intensity of emission spectra to be measured
  $I_{IR}$: intensity of background emission spectra resulting from infrared radiation
  $I_M$: intensity of emission spectra of the element being analyzed
$\lambda$: wavelength to be measured
h: Planck's constant
c: velocity of light
T: temperature at a hot spot
k: Boltzmanns constant
$\gamma(T)$: activity coefficient of the element being analyzed in molten iron
$P(T)$: vapor pressure of the element being analyzed
C: constant term in excitation and emission Accordingly, the intensity of spectra to be measured depends on the temperature at a hot spot or, in other words, is affected by temperature changes thereat. When pure oxygen is blown, the temperature at a hot spot changes with the amount of its blow. When a mixed gas containing oxygen is blown, on the other hand, the temperature thereat changes with the chemical composition and amount of the mixed gas. But changes under the same blowing condition are limited, conceivably within the limits of plus/minus 20° C. To take an example, let us consider the changes in the intensity of manganese spectrum that occurs when the temperature at a hot spot varies from 2200° C. within the limits of plus/minus 50° C. Possibly, spectral intensity may vary by approximately 50 percent maximum under the influence of the term exp $(-hc/k\lambda T)$ that contributes to infrared radiation and atomic emission. But variations due to the term $\gamma(T)$ and $P(T)$, which contribute to the vaporized quantity of the element being analyzed, are only approximately 3 percent and 10 percent maximum, respectively. In determining the object element in molten iron by a method of this invention, therefore, the intensity of background emission can be standardized by determining the intensity of emission resulting from the infrared radiation from the molten iron. By so doing, the influence of temperature changes at a hot spot can be corrected, thereby permitting a precise spectroscopic analysis.

The emission spectra from a spot locally heated by a chemical flame blown against the surface of molten iron comprises continuous emission spectra of the chemical flame, continuous spectra due to the infrared radiation from the molten iron, and emission spectra of the element being analyzed. The continuous spectra are identified as background emission in spectroscopic analysis. The intensity of the determined emission spectra can be expressed by the following equation.

$$I_{abs} = I_{Flame} + I_{IR} + I_M$$

$$= C_1 \exp(-hc/k\lambda T_1) + (2\pi hc^2/\lambda^5)\exp(-hc/k\lambda T_1) +$$

$$C_2 \cdot \gamma(T_2) \cdot P(T_2)\exp(-hc/k\lambda T_1)$$

$$= \{C_1 + 2\pi hc^2/\lambda^5 + C_2 \cdot \gamma(T_2) \cdot P(T_2)\} \exp(-hc/k\lambda T_1)$$

where
$I_{abs}$: intensity of emission spectra to be measured $I_{Flame}$: intensity of continuous emission spectra from the chemical flame $I_{IR}$: intensity of background emission spectra resulting from infrared radiation $I_M$: intensity of emission spectra of the element being analyzed $\lambda$: wavelength to be measured h: Planck's constant c: velocity of light $T_1$: temperature of the chemical flame k: Boltzmann's constant $T_2$: temperature of the molten iron in a heated region $\gamma(T_2)$: activity coefficient of the element being analyzed in molten iron $P(T_2)$: vapor pressure of the element being analyzed $C_1, C_2$: constant term in excitation and emission Accordingly, the spectral intensity to be determined depends on the temperature of the chemical flame and that of molten iron in the region heated thereby. When an air-acetylene flame of about 2200° C. is blown against molten steel of about 1600° C., for example, the temperature $T_1$ of the chemical flame depends on the chemical composition and ratio of the combustion and combustion-assisting gases used.

When the temperature of the chemical flame is sufficiently higher than that of molten iron, the temperature $T_2$ of the molten iron in the locally heated region is kept at a stable level of approximately 2000° C. In the above equation, therefore, it is possible to make constant $T_1$ by choosing an appropriate chemical flame, and $T_2$ unless the temperature of molten iron changes substantially. Consequently, infrared radiation from the molten iron can be ignored in determining the object element contained therein by the method of this invention.

A choice between the method to form a hot spot and the method to locally heat by chemical flame can be made depending on the concentration of carbon in molten iron. It is also possible, first, to produce a hot spot by blowing oxygen, and then to heat the surface of molten iron with chemical flame when carbon concentration has dropped.

If a wavelength modulator is included in a spectrometer, signal and background can be separated, thereby permitting measurement with a higher degree of precision.

For measurement of emission spectra from a hot spot or locally flame-heated area, radiations must be led to a spectrometer placed away from the spot where molten iron is present. Preferably, a spectrometer and other precision measuring instruments should be located independently and as much away from such a spot as possible, in view of the high temperature, vibration, dust and other detrimental environmental conditions that are often found in actual operation sites. Therefore, an optical system plays an important role in the transmission of radiations to the spectrometer. Such transmission may be achieved by the use of optical fibers or such aids as lens, mirrors and prisms. Optical fibers provide greater design advantage when the transmission of radiations is done over a relatively long distance.

Spectrometer in common use are of the dispersive type. But non-dispersive ones may also be used if their resolution is high enough.

Now, this invention will be described in detail by reference to the accompanying drawings. FIG. 1 shows an apparatus for use in the implementation of an analytical method of this invention that makes use of a hot spot produced by an oxygen blow in steelmaking. The apparatus essentially comprises a lance 2 to blow oxygen or an oxygen-containing mixed gas against molten iron, shown in FIG. 2, optical fibers 3 serving as an optical system to transmit radiations from a hot spot 9 to a spectrometer 10 which produces spectra from the introduced radiations. A chemical flame may also be blown from the lance 2. Oxygen gas supplied into the lance 2 through a gas inlet 4 is blow against the surface of the molten iron to produce the hot spot 9. For the purpose of hot-spot temperature control, carbon monoxide and hydrocarbon gas as well as such inert gases as argon, nitrogen and carbon dioxide may be made with oxygen. The oxygen lance 2 in the apparatus just described is of the water-cooled double-tube structure that is designed to afford protection against the radiation heat from molten steel 1. Cooling water is admitted into the lance 2 through an inlet 5 and leaves through an outlet 6.

Figure 2:
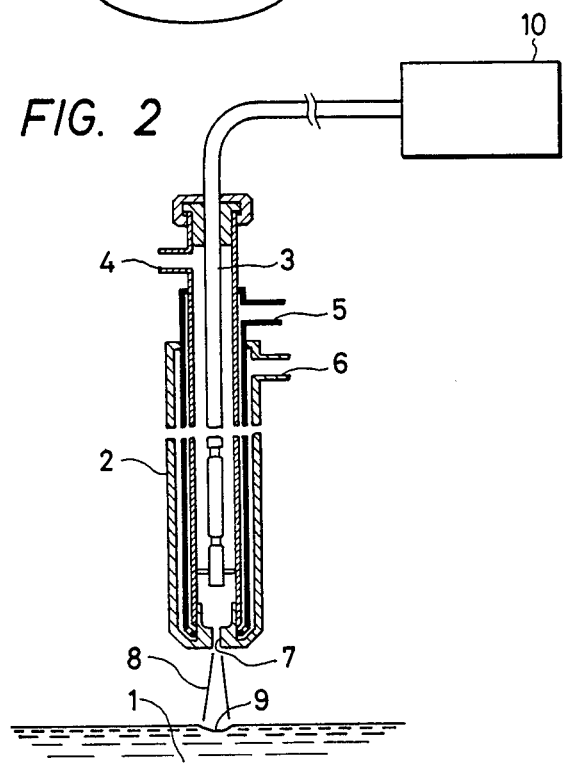
FIG. 2 is a cross-sectional view showing an example of a lance used in the operation of the analysis method according to this invention.

In the embodiment shown in FIGS. 1 and 2, the optical fibers 3 are inserted in the oxygen lance 2 of a basic oxygen converter 11. But optical fibers may be provided anywhere so long as observation of the hot spot or locally heated spot is possible. An extra lance for carrying optical fibers for observation may also be provided. Another lance to inject oxygen or an oxygen-containing mixed gas for the creation of a hot spot may be used, as well. But providing the optical fibers 3 in the oxygen lance affords protection against the radiation heat from the molten steel. It also prevents the ends of the optical fibers from getting contaminated by dust and the like liberated from the molten steel blown with oxygen or an oxygen-containing mixed gas. And the use of single lance serving dual purposes permits streamlining the whole apparatus.

Optical fibers used in the transmission of radiations to a spectrometer may be supplanted by a set of lenses. Such lenses may be placed anywhere so long as observation of the hot spot or locally heated spot is ensured. Preferably, however, they should be contained in an extra lance to permit easy maintenance and protection.

The analytical methods according to this invention which uses the heat of a hot spot or chemical flame as a source of vaporization and excitation, as with conventional spectroscopic techniques, cannot determine the contents of constituents in molten iron directly from the intensity of their emission spectra alone. As has been done conventionally, therefore, standard samples of molten iron containing different percentages of different elements are prepared beforehand. Then, a calibration curve may be prepared on the basis of the relationship between the contents of such elements in the reference samples and the intensity of their emission spectra at a hot spot or a locally flame-heated spot. The intensities of the emission spectra of individual elements may be used as they stand. In the case of molten iron, however, more accurate quantitative analysis can be achieved through the use of the ratio of the intensity of the emission spectrum of iron, which is the main constituent, to that of the emission spectrum of a particular element whose content of concentration is being sought.

EXAMPLE

The following paragraphs describe an example in which oxygen was blown against molten steel. Using the apparatus shown in FIG. 1, the content of manganese in molten steel was determined. The oxygen lance 2 containing the optical fibers 3 was set in position above the surface of the molten steel 1. To afford protection against the radiation heat from the molten steel 1, the lance 2 was of the water-cooled double-tube structure. Cooling water was supplied through the inlet 5 and discharged through the outlet 6. At the bottom end of the lance 2 (directed toward the molten steel 1) was provided an ejection port 7 through which oxygen or an oxygen-containing mixed gas was to be blown against the surface of the molten steel. Oxygen was supplied into the lance 2 through a gas supply port 4 and blown against the surface of the molten steel as a high velocity jet 8. The tip of the optical fibers 3 are directed at the hot spot 9 through the ejection port 7 so that radiations from the hot spot could be transmitted to the spectrometer 10.

In the example being described, pure oxygen was blown against the surface of the molten steel 1 through the lance 2, at a rate of 25 liter/min. Radiations from the hot spot 9 formed directly below the ejection port 7 were transmitted through the optical fibers 3 to the spectrometer 10 having a focal distance of 75 cm. The concentration of carbon in the molten steel 1 was approximately 3 percent, the temperature of the hot spot 9 ranging within the limits of 2150° C. plus/minus 20° C.

Figure 3:
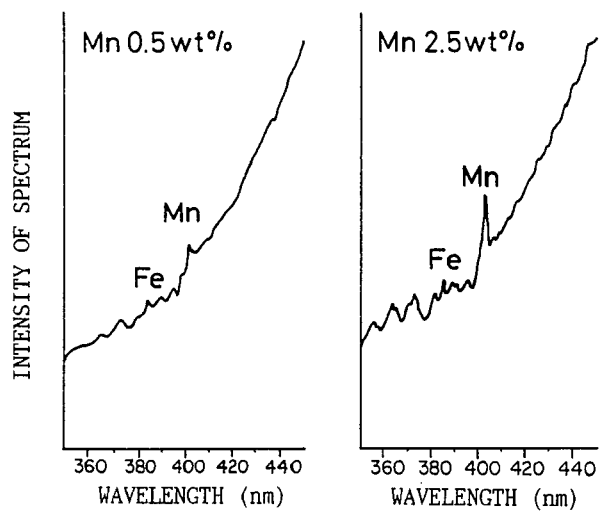
FIG. 3 graphically shows the spectra of iron and manganese observed at a hot spot produced by a method of this invention.

FIG. 3 shows the emission spectra of iron and manganese from the hot spot 9 of the molten steel 1, as determined by the analytical method of this invention. Atomic spectra of iron and manganese having wavelengths of 385.9 nm and 403.4 nm respectively were determined. The spectra were measured by high-speed scanning using self-scanned image sensors that were provided in the sensing segment of the spectrometer 10 in place of a photomultiplier.

Figure 4:
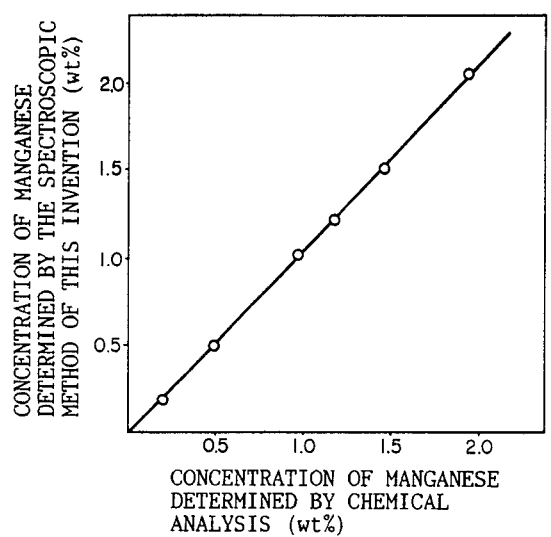
FIG. 4 graphically shows the relationship between the concentration of manganese determined by a method embodying the principle of this invention and that determined by chemical analysis of sample collected from the molten iron analyzed.

FIG. 4 compares the concentration of manganese determined by the spectroscopic method of this invention and that which was determined by chemical analysis applied to a sample taken from the same molten steel. The two analytical values gave excellent agreement, proving the applicability of the spectroscopic method of this invention to the determination of manganese content in molten steel.

Because of the measuring principle involved, the spectroscopic method of this invention is applicable to the determination of such elements as will vaporize from the molten steel at a temperature of hot sport, emitting radiations. However, it is practically inapplicable to the determination of such elements as nitrogen, oxygen, sulphur and phosphorus whose main emission spectra are in the vacuum ultraviolet region.

Figure 5:
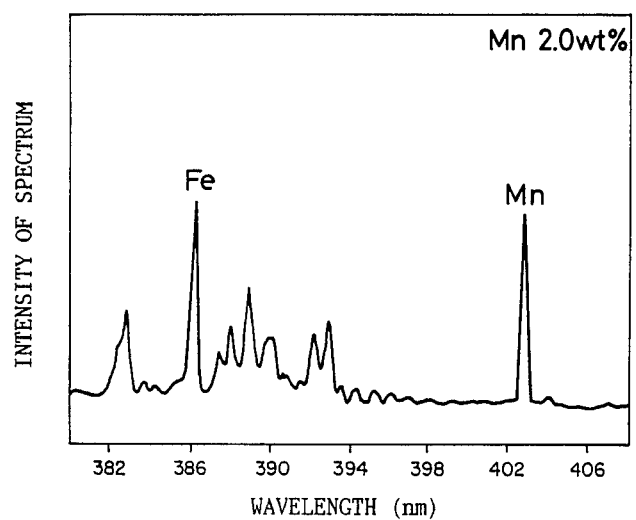
FIG. 5 is a graph in which the emission spectra of iron and manganese produced by blowing a chemical flame are plotted.

FIG. 5 shows the emission spectra of iron and manganese determined with the use of chemical flame. As with the spectroscopy using a hot spot, calibration curves can be prepared based on the data obtained from samples containing different concentrations of elements.

What is claimed is:

1. A method of spectroscopically determining the composition of molten iron which comprises the steps of producing a hot spot by blowing oxygen or an oxygen-containing mixed gas against the surface of the molten iron and measuring the spectra of radiations emitted from the hot spot.

2. A method of spectroscopically determining the composition of molten iron according to claim 1, in which the radiations from the hot spot are transmitted to a spectrometer for analysis through optical fibers.

3. A method of spectroscopically determining the composition of molten iron according to claim 2, in which the optical fibers are provided in a lance through which oxygen or an oxygen-containing mixed gas is blown, the tip of the optical fibers being directed toward the hot spot.

4. A method of spectroscopically determining the composition of molten iron according to claim 1, in which the radiations from the hot spot are transmitted to a spectrometer for analysis through a set of lenses.

5. A method of spectroscopically determining the composition of molten iron according to claim 1, in which the molten iron is contained in a basic oxygen converter.

6. A method of spectroscopically determining the composition of molten iron which comprises the steps of heating a localized area in the surface of molten iron with a chemical flame blown thereagainst, the chemical flame being produced by a mixture of a combustion gas and a combustion-assisting gas, and measuring the spectra of radiations emitted from the locally heated area.

7. A method of spectroscopically determining the composition of molten iron according to claim 6, in which the radiations from the locally heated area are transmitted to a spectrometer for analysis through optical fibers.

8. A method of spectroscopically determining the composition of molten iron according to claim 7, in which the optical fibers are provided in a lance through which a chemical flame is blown, the tip of the optical fibers being directed toward the locally heated area.

9. A method of spectroscopically determining the composition of molten iron according to claim 6, in which the radiations from the locally heated area are transmitted to a spectrometer for analysis through a set of lenses.

* * * * *